United States Patent
Yamada et al.

(10) Patent No.: US 9,265,256 B2
(45) Date of Patent: Feb. 23, 2016

(54) PEST CONTROL COMPOSITION

(75) Inventors: Masahiro Yamada, Toyonaka (JP); Yoshito Tanaka, Toyonaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 424 days.

(21) Appl. No.: 13/508,484

(22) PCT Filed: Nov. 19, 2010

(86) PCT No.: PCT/JP2010/071197
§ 371 (c)(1),
(2), (4) Date: May 7, 2012

(87) PCT Pub. No.: WO2011/062299
PCT Pub. Date: May 26, 2011

(65) Prior Publication Data
US 2012/0225917 A1 Sep. 6, 2012

(30) Foreign Application Priority Data
Nov. 20, 2009 (JP) ................................. 2009-264781

(51) Int. Cl.
*A61K 31/21* (2006.01)
*A61K 31/26* (2006.01)
*A01N 53/00* (2006.01)

(52) U.S. Cl.
CPC ...................................... *A01N 53/00* (2013.01)

(58) Field of Classification Search
CPC ...... A01N 25/006; A01N 29/00; A01N 29/04
USPC ......................................................... 514/529
See application file for complete search history.

(56) References Cited

U.S. PATENT DOCUMENTS

| 4,595,679 | A | 6/1986 | Broadbent | |
|---|---|---|---|---|
| 5,733,478 | A * | 3/1998 | Creech et al. | 252/400.21 |
| 6,555,092 | B2 * | 4/2003 | Sembo et al. | 424/45 |
| 8,114,897 | B2 | 2/2012 | Sembo | |
| 2002/0147179 | A1 | 10/2002 | Munagavalasa et al. | |
| 2003/0195119 | A1 * | 10/2003 | Mori | 504/309 |
| 2004/0106523 | A1 | 6/2004 | Stridde et al. | |
| 2005/0038094 | A1 * | 2/2005 | Warrington | 514/383 |
| 2005/0074475 | A1 * | 4/2005 | Southworth | 424/405 |
| 2008/0255204 | A1 | 10/2008 | Davies et al. | |
| 2009/0105073 | A1 | 4/2009 | Taranta et al. | |
| 2010/0048700 | A1 | 2/2010 | Davies et al. | |

FOREIGN PATENT DOCUMENTS

| CN | 1451650 | A | 10/2003 |
|---|---|---|---|
| CN | 1942095 | A | 4/2007 |
| CN | 101460052 | A | 6/2009 |
| CN | 101494984 | A | 7/2009 |
| JP | 11-322516 | A | 11/1999 |
| JP | 2003-327502 | A | 11/2003 |
| JP | 2004-2363 | A | 1/2004 |
| JP | 2004-523499 | A | 8/2004 |
| JP | 2008-201731 | A | 9/2008 |
| WO | WO 2005/096815 | A1 | 10/2005 |
| WO | WO 2008/006464 | A1 | 1/2008 |
| WO | WO 2009/006464 | A1 | 1/2009 |
| WO | WO 2009/031692 | A2 | 3/2009 |
| WO | WO 2009/031697 | A2 | 3/2009 |
| WO | WO 2009/126577 | A2 | 10/2009 |

OTHER PUBLICATIONS

The Communication Pursuant to Article 94(3) EPC, dated Apr. 22, 2014, issued in the corresponding European Patent Application No. 10831685.2.
The Second Office Action and Search Report (including English translation), dated Apr. 22, 2014, issued in the corresponding Chinese Patent Application No. 201080052067.X.
The Office Action (including an English translation), dated Jun. 24, 2014, issued in the corresponding Japanese Patent Application No. 2010-257548.
The Patent Examination Report No. 1, dated Jun. 10, 2014, issued in the corresponding Australian Patent Application No. 2010322724.
International Preliminary Report on Patentability and Written Opinion of the International Searching Authority dated May 22, 2012, for Application No. PCT/JP2010/071197.
Extended European Search Report for European Application No. 10831685.2, dated Aug. 28, 2013.

(Continued)

*Primary Examiner* — San-Ming Hui
(74) *Attorney, Agent, or Firm* — Birch, Stewart, Kolasch & Birch, LLP

(57) ABSTRACT

The present invention provides a pest control composition having an excellent controlling effect on pests, which comprises a combination of an ester compound represented by the formula (1): and a cyclic compound represented by the formula (2a) and/or a cyclic compound represented by the formula (2b).

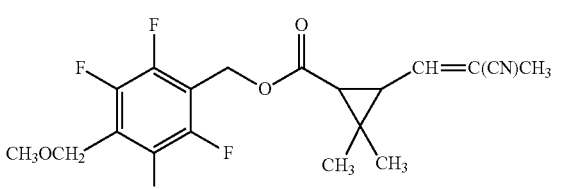

(1)

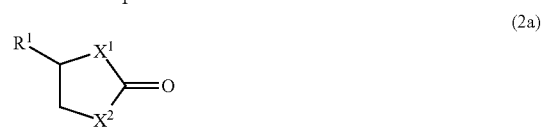

(2a)

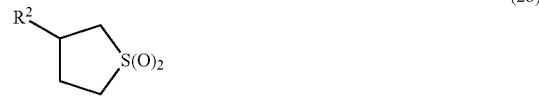

(2b)

7 Claims, No Drawings

(56) References Cited

OTHER PUBLICATIONS

International Search Report, dated Jan. 25, 2011, issued in PCT/JP2010/071197.
Written Opinion of the International Searching Authority, dated Jan. 25, 2011, issued in PCT/JP2010/071197.
Chinese Office Action for Chinese Application No. 201080052067.X with English translation, issued May 30, 2013.
The Office Action (including an English translation), dated Aug. 29, 2014, issued in the corresponding Taiwanese Patent Application No. 099139878.
The Third Office Action (including an English translation), dated Nov. 18, 2014, issued in the corresponding Chinese Patent Application No. 201080052067.X.
The Communication pursuant to Article 94(3) EPC, dated Jan. 29, 2015, issued in the corresponding European Patent Application No. 10831685.2.
An Office Action (including an English translation thereof) issued in the corresponding Mexican Patent Application No. MX/a/2012/005630 on Jun. 29, 2015.
The Office Action (including an English translation), dated Mar. 9, 2015, issued in the corresponding Taiwanese Patent Application No. 099139878.
European Patent Office Communication pursuant to Article 94(3) EPC issued in the corresponding European Patent Application No. 10831685.2 on Nov. 24, 2015.

* cited by examiner

PEST CONTROL COMPOSITION

TECHNICAL FIELD

The present invention relates to a pest control composition and a control method of pests.

BACKGROUND ART

An ester compound represented by the formula (1):

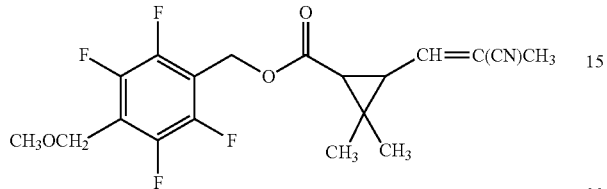

is known to have an pest controlling effect, and it is also known that the ester compound can be used in combination or admixture with a synergist such as piperonyl butoxide (see e.g., Patent Literature 1).

CITATION LIST

Patent Literature

Patent Literature 1: JP-A 2004-2363

SUMMARY OF INVENTION

Technical Problem

An object of the present invention is to provide a pest control composition and a control method of pests having an excellent control effect on pests.

Solution to Problem

The present inventors studied intensively to find a pest control composition having an excellent control effect on pests. As a result, the present invention was completed.

The present invention includes:
(1) A pest control composition containing a combination of an ester compound represented by the formula (1):

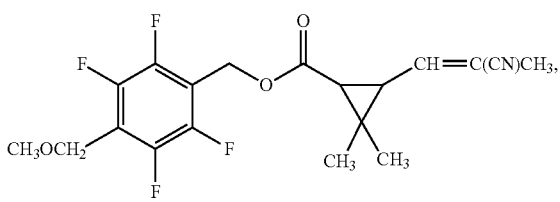

and a cyclic compound represented by the formula (2a):

[wherein $X^1$ represents an oxygen atom or a C1-C8 alkylimino group, $X^2$ represents a methylene group, an oxygen atom or a C1-C8 alkylimino group, and $R^1$ represents a hydrogen atom or a methyl group], and/or a cyclic compound represented by the formula (2b):

[wherein $R^2$ represents a hydrogen atom or a methyl group];
(2) A pest control composition containing a combination of an ester compound represented by the formula (1):

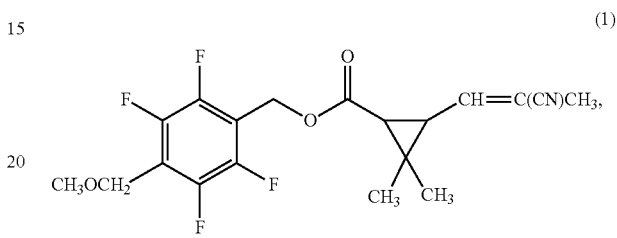

and a cyclic compound represented by the formula (2a):

[wherein $X^1$ represents an oxygen atom or a C1-C8 alkylimino group, $X^2$ represents a methylene group, an oxygen atom or a C1-C8 alkylimino group, and $R^1$ represents a hydrogen atom or a methyl group];
(3) The pest control composition according to the above (1) or (2), wherein the weight ratio of the ester compound to the cyclic compound(s) is within the range of from 4:1 to 1:300;
(4) The pest control composition according to the above (1) or (2), wherein the weight ratio of the ester compound to the cyclic compound(s) is within the range of from 1:1 to 1:100; and
(5) A control method of pests which comprises applying the pest control composition according to any one of the above (1) to (4) to the pests or areas where the pests live.

Effects of Invention

Pests can be controlled by using the pest control composition of the present invention.

DESCRIPTION OF EMBODIMENTS

The ester compound represented by the formula (1) (hereinafter, referred to as a present ester compound) can be produced, for example, by a process described in JP-A 2004-2363.

The present ester compound has isomers based on two asymmetric carbon atoms on the cyclopropane ring and based on a double bond of a substituent on the cyclopropane ring. In the present invention, the ester compound containing the active isomers in any ratios can be used.

Examples of the present ester compound include:
[2,3,5,6-tetrafluoro-4-(methoxymethyl)phenyl]methyl (1R)-3-(2-cyano-1-propenyl)-2,2-dimethylcyclopropanecarboxylate,

[2,3,5,6-tetrafluoro-4-(methoxymethyl)phenyl]methyl (1R)-trans-3-(2-cyano-1-propenyl)-2,2-dimethylcyclopropanecarboxylate,

[2,3,5,6-tetrafluoro-4-(methoxymethyl)phenyl]methyl (1R)-cis-3-(2-cyano-1-propenyl)-2,2-dimethylcyclopropanecarboxylate,

[2,3,5,6-tetrafluoro-4-(methoxymethyl)phenyl]methyl (1R)-trans-3-((E)-2-cyano-1-propenyl)-2,2-dimethylcyclopropanecarboxylate, and

[2,3,5,6-tetrafluoro-4-(methoxymethyl)phenyl]methyl (1R)-trans-3-((Z)-2-cyano-1-propenyl)-2,2-dimethylcyclopropanecarboxylate.

In the formula (2a), $X^1$ represents an oxygen atom or a C1-C8 alkylimino group, $X^2$ represents a methylene group, an oxygen atom or a C1-C8 alkylimino group, and $R^1$ represents a hydrogen atom or a methyl group When $X^1$ is an oxygen atom, $X^2$ is preferably a methylene group or a C1-C8 alkylimino group.

When $X^1$ is a C1-C8 alkylimino group, $X^2$ is preferably an oxygen atom or a C1-C8 alkylimino group.

When $X^2$ is a methylene group, $X^1$ is preferably an oxygen atom or a C2-C8 alkylimino group.

In the formula (2a), examples of the "C1-C8 alkylimino group" represented by $X^1$ or $X^2$ include a methylimino group, an ethylimino group, a propylimino group, a butylimino group, a pentylimino group, a hexylimlno group, a heptylimino group and an octylimino group.

The cyclic compounds represented by the formula (2a) and (2b) (hereinafter, referred to as a present cyclic compound), for example, are commercially available.

Examples of the present cyclic compound represented by the formula (2a) include the following compounds:

A compound of the formula (2a) wherein $X^1$ is an oxygen atom and $X^2$ is a methylene group;

A compound of the formula (2a) wherein $X^1$ is an oxygen atom and $X^2$ is an oxygen atom;

A compound of the formula (2a) wherein $X^1$ is an oxygen atom and $X^2$ is a C1-C8 alkylimino group;

A compound of the formula (2a) wherein $X^1$ is a C1-C8 alkylimino group and $X^2$ is a methylene group;

A compound of the formula (2a) wherein $X^1$ is a C1-C8 alkylimino group and $X^2$ is an oxygen atom;

A compound of the formula (2a) wherein $X^1$ is a C1-C8 alkylimino group and $X^2$ is a C1-C8 alkylimino group;

A compound of the formula (2a) wherein $X^1$ is an oxygen atom and $X^2$ is a methylene group or a C1-C8 alkylimino group;

A compound of the formula (2a) wherein $X^1$ is a C1-C8 alkylimino group and $X^2$ is an oxygen atom or a C1-C8 alkylimino group;

(i) γ-butyrolactone (i.e., a compound of the formula (2a) wherein $X^1$ is an oxygen atom, $X^2$ is a methylene group, and $R^1$ is a hydrogen atom);

(ii) N-methyl-2-pyrrolidone (i.e., a compound of the formula (2a) wherein $X^1$ is a methylimino group, $X^2$ is a methylene group, and $R^1$ is a hydrogen atom);

(iii) N-ethyl-2-pyrrolidone (i.e., a compound of the formula (2a) wherein $X^1$ is an ethylimino group, $X^2$ is a methylene group, and $R^1$ is a hydrogen atom);

(iv) N-octyl-2-pyrrolidone (i.e., a compound of the formula (2a) wherein $X^1$ is an octylimino group, $X^2$ is a methylene group, and $R^1$ is a hydrogen atom);

(v) 1,3-Dimethyl-2-imidazolidinone (i.e., a compound of the formula (2a) wherein $X^1$ is a methylimino group, $X^2$ is a methylimino group, and $R^1$ is a hydrogen atom);

(vi) Propylene carbonate (i.e., a compound of the formula (2a) wherein $X^1$ is an oxygen atom, $X^2$ is an oxygen atom, and $R^1$ is a methyl group); and (vii) Ethylene carbonate (i.e., a compound of the formula (2a) wherein $X^1$ is an oxygen atom, $X^2$ is an oxygen atom, and $R^1$ is a hydrogen atom).

Examples of the present cyclic compound represented by the formula (2b) include the following compound:

(viii) Sulfolane (i.e., a compound of the formula (2b) wherein $R^2$ is a hydrogen atom).

The pest control composition of the present invention may contain one or more kinds of the present cyclic compounds.

Examples of pests against which the pest control composition of the present invention exhibits a controlling effect (insecticidal effect, knock down effect, repellent effect, etc.) include harmful arthropods such as insect pests and acarine pests. Specific examples thereof are as follows.

Lepidoptera Insect Pests:

Pyralid moths (Pyralidae) such as rice stem borer (*Chilo suppressalis*), rice leafroller (*Cnaphalocrocis medinalis*), and Indian meal moth (*Plodia interpunctella*); owlet moths (Noctuidae) such as common cutworm (*Spodoptera litura*), beet armyworm (*Spodoptera exigua*), rice armyworm (*Pseudaletia separate*), and cabbage armyworm (*Mamestra brassicae*); white butterflies (Pieridae) such as common white (*Pieris rapae*); tortricid moths (Tortricidae) such as *Adoxophyes* spp.; fruitworm moths (Carposinidae); lyonetiid moths (Lyonetiidae); tussock moths (Lymantriidae); *Plusiae*; *Agrotis* spp. such as cutworm (*Agrotis segetum*) and bluck cutworm (*Agrotis ipsilon*); *Helicoverpa* spp.; *Heliothis* spp.; diamondback (*Plutella xylostella*); common straight swift (*Pamara guttata*); casemaking clothes moth (*Tinea translucens*); and webbing clothes moth (*Tineola bisselliella*).

Diptera Insect Pests:

Mosquitos (Calicidae) such as common house mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; midges (Chironomidae); houseflies (Muscidae) such as housefly (*Musca domestica*), false stable fly (*Muscina stabulans*), and lesser housefly (*Fannia canicularis*); blow flies (Calliphoridae); flesh flies (Sarcophagidae); anthomyiid flies (Anthomyiidae) such as seedcorn maggot (*Delia platura*), and onion maggot (*Delia antiqua*); fruit flies (Tephritidae); leaf-miner flies (Agromyzidae); small fruit flies (Drosophilidae); moth flies (Psychodidae); Phorid flies (Phoridae); black flies (Simuliidae); horse flies (Tabanidae); stable flies (Stomoxyidae); and biting midges (Ceratopogonidae).

Dictyoptera Insect Pests:

Cockroaches (Blattariae) such as German cockroach (*Blattella germanica*), smokybrown cockroach (*Periplaneta fuliginosa*), American cockroach (*Periplaneta americana*), blown cockroach (*Periplaneta brunnea*), and oriental cockroach (*Blatta orientalis*).

Hymenoptera Insect Pests:

Ants (Formicidae); hornets (Vespidae); Bethylid wasps (Betylidae); and sawflies (Tenthredinidae) such as cabbage sawfly (*Athalia rosae*).

Aphaniptera Insect Pests:

Dog flea (*Ctenocephalides canis*), cat flea (*Ctenocephalides feils*), and human flea (*Purex irritans*).

Anoplura Insect Pests:

Human louse (*Pediculus humans*), crab louse (*Phthirus pubis*), head louse (*Pediculus humans capitis*), and human body louse (*Pediculus humanus corporis*).

Isoptera Insect Pests:

Japanese subterranean termite (*Reticulitermes speratus*), and Formosan subterranean termite (*Coptotermes formosanus*).

Hemiptera Insect Pests:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), and Taiwan green rice leafhopper (*Nephotettix virescens*); aphids (Aphididae); stink bugs (Pentatomidae); whiteflies (Aleyrodidae); scales (Coccidae); cimices such as *Cimex lectularius*; lace bugs (Tingidae); and psyllids (Psyllidae).

Coleoptera Insect Pests:

Corn root worms (*Diabrotica* spp.) such as black carpet beetle (*Attagenus japonicus*), varied carpet beetle (*Anthreus verbasci*), Western corn root worm (*Diabrotica virgifera virgifera*), and Southern corn root worm (*Diabrotica undecimpunctata howardi*); scarabs (Scarabaeidae) such as cupreous chafer (*Anomala cuprea*), and soybean beetle (*Anomala rufocuprea*); weevils (Curculionidae) such as maize weevil (*Sitophilus zeamais*), rice water weevil (*Lissorhoptrus oryzophilus*), boll weevil (*Anthonomus grandis*), and azuki bean weevil (*Callosobruchus chinensis*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), striped flea beetle (*Phyllotreta striolata*), and cucurbit leaf beetle (*Aulacophora femoralis*); drugstore beetles (Anobiidae); *Epilachna* spp. such as twenty-eight-spotted ladybird (*Epilachna vigintioctopunctata*); powder post beetles (Lyctinae); false powder post beetles (Bostrichadae); longhorn beetles (Cerambycidae); and rove beetle (*Paederus fuscipes*).

Thysanoptera Insect Pests:

Melon *thrips* (*Thrips palmi*), yellow citrus *thrips* (*Frankliniella occidentalis*), and flower *thrips* (*Frankliniella intonsa*).

Orthoptera Insect Pests:

Mole crickets (Gryllotalpidae), and grasshoppers (Acrididae).

Acarina:

House dust mites (Pyroglyphidae) such as *Dermatophagoides farinae*, and *Dermatophagoides ptrenyssnus*; Acarid mites (Acaridae) such as mold mite (*Tyrophagus putrescentiae*), and *Aleuroglyphus ovatus*; Glycyphagid mites such as *Glycyphagus privatus, Glycyphagus domesticus*, and *Glycyphagus destructgor*; Cheyletide mites (Cheyletidae) such as *Cheyletus malaccensis*, and *Cheyletus fortis*; Tarsonemid mites (Tarsonemidae); Chortoglyphid mites (Chortoglyphidae); Haplochthoniid mites (Haplochthoniidae); spider mites (Tetranychidae) such as two-spotted spider mite (*Tetranychus urticae*), Kanzawa spider mite (*Tetranychus kanzawai*), citrus red mite (*Panonychus citri*), and European red mite (*Panonychus ulmi*); ticks (Ixodidae) such as *Haemaphysalis longicornis*; and parasitoid mites (Dermanyssidae) such as northern fowl mite (*Ornithonyssus sylviarum*), and poultry red mite (*Dermanyssus gallinae*).

In particular, the pest control composition of the present invention exhibits excellent controlling effect on Diptera insect pests, Dictyoptera pests, and Hymenoptera pests.

In the pest control composition of the present invention, the weight ratio of the present ester compound to the present cyclic compound is within the range of usually from 4:1 to 1:300, preferably from 3:1 to 1:200, more preferably from 1:1 to 1:100, further more preferably from 1:2 to 1:100, and still further more preferably from 1:3 to 1:100. When two or more kinds of the present cyclic compounds are contained in the pest control composition of the present invention, the ratio of the weight of the present ester compound to the total weight of the present cyclic compounds is within the above-mentioned range.

The pest control composition of the present invention can be a simple mixture of the present ester compound and the present cyclic compound(s). However, it is usually used in the form of various formulations. Examples of the formulations include soluble concentrate, oil solution, emulsifiable concentrate, wettable powder, suspension concentrate (e.g. suspension in water, and emulsion in water), microcapsule formulation, dust, granule, tablet, aerosol, carbon dioxide formulation, heating vaporization formulation (e.g. mosquito coil, electric mosquito mat, and fluid absorption wicking-type pesticide), piezo-type spray insecticide, heating fumigant (e.g. self-burning fumigant, chemical reaction type fumigant, and porous ceramic plate fumigant), non-heating fumigant (e.g. resin fumigant, paper fumigant, unwoven fabric fumigant, woven fabric fumigant, and sublimation tablet), smoking formulation (e.g. fogging), direct contact formulation (e.g. sheet type contact formulation, tape type contact formulation, and net type contact formulation), ULV formulation, and poison bait.

The formulation can be prepared, for example, by the following methods (1) to (3).

(1) The present ester compound and the present cyclic compound(s) are mixed with a solid carrier, a liquid carrier, a gaseous carrier or feed and, if necessary, other auxiliary agents for formulations such as a surfactant.

(2) A base material containing no active ingredient is impregnated with a mixture of the present ester compound and the present cyclic compound(s).

(3) The present ester compound, the present cyclic compound(s) and a base material are mixed, followed by molding.

These formulations usually contain as a total amount 0.001 to 98% by weight of the present ester compound and the present cyclic compound(s).

Examples of the solid carrier used for the formulation include fine powders and granules such as clays (e.g. kaolin clay, diatomaceous earth, bentonite, Fubasami clay, and acidic white clay), synthetic hydrated silicon oxide, talc, ceramics, other inorganic minerals (e.g. sericite, quarts, sulfur, active carbon, calcium carbonate, and hydrated silica), and chemical fertilizers (e.g. ammonium sulfate, ammonium phosphate, ammonium nitrate, ammonium chloride, and urea); and solid materials at ordinary temperature (e.g. 2,4,6-triisopropyl-1,3,5-trioxane, naphthalene, p-dichlorobenzene, camphor, and adamantane) as well as felt, fibers, cloth, woven fabrics, sheets, paper, threads, foam, porous materials and multifilaments composed of one or more of wool, silk, cotton, hemp, pulp, synthetic resins (e.g. polyethylene resins such as low-density polyethylene, linear low-density polyethylene, and high-density polyethylene; ethylene-vinyl ester copolymers such as ethylene-vinyl acetate copolymer; ethylene-methacrylate copolymers such as ethylene-methyl methacrylate copolymer, and ethylene-ethyl methacrylate copolymer; ethylene-acrylate copolymers such as ethylene-methyl acrylate copolymer, and ethylene-ethyl acrylate copolymer; ethylene-vinyl carboxylate copolymers such as ethylene-acrylic acid copolymer; ethylene-tetracyclododecene copolymer; polypropylene resins such as propylene homopolymer, and propylene-ethylene copolymer; poly-4-methylpentene-1; polybutene-1; polybutadiene; polystyrene; acrylonitrile-styrene resin; styrene elastomers such as acrylonitrile-butadiene-styrene resin, styrene-conjugated diene block copolymer, and hydrogenated styrene-conjugated diene block copolymer; fluorine plastics; acrylic resins such as polymethyl methacrylate; polyamide resins such as nylon 6, and nylon 66; polyester resins such as polyethylene terephthalate, polyethylene naphthalate, polybutylene terephthalate, and polycyclohexylene dimethyleneterephthalate; polycarbonate; polyacetal; polyacrylsulfone; polyarylate; polyhydroxybenzoate; polyetherimide; polyestercarbonate; polyphenylene ether resin; polyvinyl chloride; polyvinylidene chloride; polyurethane; and porous resins such as foamed polyurethane, foamed polypropylene, and foamed polyethylene), glass, metals, and ceramics.

Examples of the liquid carrier include aromatic or aliphatic hydrocarbons (e.g. xylene, toluene, alkyl naphthalene, phenylxylylethane, kerosene, light oil, hexane, and cyclohexane), halogenated hydrocarbons (e.g. chlorobenzene, dichloromethane, dichloroethane, and trichloroethane), alcohols (e.g. methanol, ethanol, isopropyl alcohol, butanol, hexanol, benzyl alcohol, and ethylene glycol), ethers (e.g. diethylether, ethylene glycol dimethyl ether, diethylene glycol monomethyl ether, diethylene glycol monoethyl ether, propylene glycol monomethyl ether, tetrahydrofuran, and dioxane), esters (e.g. ethyl acetate, and butyl acetate), ketones (e.g. acetone, methyl ethyl ketone, methyl isobutyl ketone, and cyclohexanone), vegetable oils (e.g. soybean oil, and cotton oil), vegetable essential oil (e.g. orange oil, hyssop oil, and lemon oil) and water.

Examples of the gaseous carrier include butane gas, chlorofluorocarbon gas, liquefied petroleum gas (LPG), dimethyl ether, and carbon dioxide.

Examples of the surfactant include alkyl sulfate ester salts, alkyl sulfonates, alkylaryl sulfonates, alkylaryl ethers, polyoxyethylenated alkylaryl ethers, sorbitan fatty acid esters, polyoxyethylene sorbitan fatty acid esters, olyethylene glycol ethers, polyhydric alcohol esters, and sugar alcohol derivatives.

Examples of other auxiliary agents for formulations include binders, dispersants, and stabilizers. Specific examples thereof include casein, gelatin, polysaccharides (e.g. starch, gum arabic, cellulose derivatives, and arginic acid), lignin derivatives, bentonite, saccharides, synthetic water-soluble polymers (e.g. polyvinyl alcohol, polyvinyl pyrrolidone, and polyacrylic acid), BHT (2,6-di-t-butyl-4-methylphenol), and BHA (mixture of 2-t-butyl-4-methoxyphenol and 3-t-butyl-4-methoxyphenol).

Examples of the base material of a mosquito coil include a mixture of plant powder (e.g. wood powder, and pyrethrum) and a binder (e.g. powder of *Machilus thunbergii,* starch, and gluten).

Examples of the base material of an electric mosquito mat include cotton linter matted, condensed and pressed in a plate shape, and mixed fibrils of cotton linter and pulp matted, condensed and pressed in a plate shape.

Examples of the base material of a self-burning fumigant include combustion heat-developing agents such as nitrates, nitrites, guanidine salts, potassium chlorate, nitrocellulose, ethyl cellulose, and wood powder; heat decomposition stimulating agents such as alkali metal salts, alkaline earth metal salts, bichromates, and chromates; oxygen suppliers such as potassium nitrate; combustion supporting agents such as melamine, and wheat starch; fillers such as diatomaceous earth; and binders such as synthetic adhesives.

Examples of the base material of a chemical reaction type fumigant include heat-developing agents such as sulfide, polysulfide, and hydrosulfide of alkali metals, and calcium oxide; catalysts such as carbonaceous materials, iron carbide, and activated clay; organic foaming agents such as azodicarbonamide, benzenesulfonyl hydrazide, dinitro pentamethylene tetramine, polystyrene and polyurethane; and fillers such as natural fibers and synthetic fibers.

Examples of the resin used for, for example, a resin fumigant include polyethylene resins such as low-density polyethylene, linear low-density polyethylene, and high-density polyethylene; ethylene-vinyl ester copolymers such as ethylene-vinyl acetate copolymer; ethylene-methacrylate copolymers such as ethylene-methyl methacrylate copolymer, and ethylene-ethyl methacrylate copolymer; ethylene-acrylate copolymers such as ethylene-methyl acrylate copolymer, and ethylene-ethyl acrylate copolymer; ethylene-vinyl carboxylate copolymers such as ethylene-acrylic acid copolymer; ethylene-tetracyclododecene copolymer; polypropylene resins such as propylene homopolymer, and propylene-ethylene copolymer; poly-4-methylpentene-1; polybutene-1; polybutadiene; polystyrene; acrylonitrile-styrene resin; styrene elastomers such as acrylonitrile-butadiene-styrene resin, styrene-conjugated diene block copolymer, and hydrogenated styrene-conjugated diene block copolymer; fluorine plastics; acrylic resins such as polymethyl methacrylate; polyamide resins such as nylon 6, and nylon 66; polyester resins such as polyethylene terephthalate, polyethylene naphthalate, polybutylene terephthalate, and polycyclohexylene dimethyleneterephthalate; polycarbonate; polyacetal; polyacrylsulfone; polyarylate; polyhydroxybenzoate; polyetherimide; polyestercarbonate; polyphenylene ether resin; polyvinyl chloride; polyvinylidene chloride; and polyurethane. They can be used alone or in a combination thereof. Further, if necessary, plasticizer such as phthalates (e.g. dimethyl phthalate, and dioctyl phthalate), adipates, and stearic acid can be added to these base materials. The resin fumigant is prepared by kneading the present ester compound and the present cyclic compound(s) into the base material, followed by molding it by injection molding, extrusion molding or press molding. The resultant resin formulation can undergo further processes such as molding and cutting, if necessary, processing into a form of plate, film, tape, net or string. These resin formulations can be processed into, for example, collars for animals, ear tags for animals, sheet formulations, guide strings and horticultural supports.

Examples of the base material for poison bait include feed ingredients such as grain powder, vegetable oil, sugars, and crystalline cellulose; antioxidants such as dibutylhydroxy toluene, and nordihydroguaiaretic acid; preservatives such as dehydroacetic acid; accidental ingestion prevention agents by children and pets such as chili pepper; and pest attractive flavors such as cheese flavor, onion flavor, and peanut oil.

The pest control composition of the present invention may be used in combination with or as a mixture with other pest control agents, repellents, or synergists.

Examples of an active ingredient of the pest control agent include the following ingredients.

(1) Synthetic pyrethroid compounds:

Acrinathrin, allethrin, beta-cyfluthrin, bifenthrin, cycloprothrin, cyfulthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, [2,3,5,6-tetrafluoro-4-(methoxymethyl)phenyl]methyl 2,2-dimethyl-3-(1-propenyl)cyclopropanecarboxylate, [2,3,5,6-tetrafluoro-4-methylphenyl]methyl 2,2-dimethyl-3-(1-propenyl)cyclopropanecarboxylate, [2,3,5,6-tetrafluoro-4-(methoxymethyl)phenyl]methyl 2,2-dimethyl-3-(2-methyl- 1-propenyl)cyclopropanecarboxylate, [2,3,5,6-tetrafluoro-4-(methoxymethyl)phenyl]methyl 2,2,3,3-tetramethylcyclopropanecarboxylate, etc.

(2) Organic Phosphorus Compounds:

Acephate, aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, etc.

(3) Carbamate Compounds:

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, etc.

(4) Nereistoxin Compounds:

Cartap, bensultap, thiocyclam, monosultap, bisultap, etc.

(5) Neonicotinoid Compounds:

Imidacloprid, nitenpyram, acetamiprid, thiamethoxam, thiacloprid, dinotefuran, clothianidin, etc.

(6) Benzoylurea Compounds:

Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, etc.

(7) Phenylpyrazole Compounds:

Acetoprole, ethiprole, fipronil, vaniliprole, pyriprole, pyrafluprole, etc.

(8) Bt Toxin Insecticides:

Live spores or crystal toxins originated from *Bacillus* thuringiesis and a mixture thereof.

(9) Hydrazine Compounds:

Chromafenozide, halofenozide, methoxyfenozide, tebufenozide, etc.

(10) Organic Chlorine Compounds:

Aldrin, dieldrin, dienochlor, endosulfan, methoxychlor, etc.

(11) Natural Insecticides:

Machine oil, nicotine-sulfate.

(12) Other Insecticides:

Avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, etc.

Examples of an active ingredient of the repellent include N,N-diethyl-m-toluamide, limonene, linalocl, citronellal, menthol, menthone, hinokitiol, geraniol, eucalyptol, indoxacarb, carane-3,4-diol, MGK-R-326, MGK-R-874 and BAY-KBR-3023.

Examples of the synergist include 5-[2-(2-butoxyethoxy)ethoxymethyl]-6-propyl-1,3-benzodioxole, N-(2-ethylhexyl)bicyclo[2.2.1]hept-5-ene-2,3-dicarboxyimide, octachlorodipropyl ether, isobornyl thiocyanoacetate, and N-(2-ethylhexyl)-1-isopropyl-4-methylbicyclo[2.2.2]oct-5-ene-2,3-dicarboxyimide.

The control method of pests of the present invention is carried out by applying the pest control composition of the present invention to pests and/or to areas where pests live (e.g., plant body, soil, indoor, and animal body).

Specifically, as an application method of the pest control composition of the present invention, the following methods can be exemplified, and these methods can be appropriately selected according to, for example, the form of the pest control composition, and the application place.

(1) The pest control composition of the present invention is applied as it is to pests and/or areas where pests live.

(2) The pest control composition of the present invention is diluted with a solvent such as water, followed by applying to pests and/or areas where pests live.

In this case, usually, the pest control composition of the present invention in the form of, for example, an emulsifiable concentrate, a wettable powder, a suspension concentrate or a microcapsule preparation is diluted so that the total concentration of the present ester compound and the present cyclic compound(s) becomes 0.01 to 1000 ppm.

(3) The pest control composition of the present invention is heated at areas where pests live to vaporize the effective ingredients.

In this case, the applied rate and concentration of the present ester compound and the present cyclic compound(s) can be appropriately determined according to, for example, the form of the pest control composition of the present invention, the application period, the application place, the application method, the kinds of pests, and the conditions of damage.

In utilizing the pest control composition of the present invention for preventative purpose, the application rate is usually from 0.0001 to 1000 mg/m$^3$ in terms of the total amount of the present ester compound and the present cyclic compound(s) when applied to space, while it is from 0.0001 to 1000 mg/m$^2$ when applied to plane. The heating vaporization formulation such as mosquito coil and electric mosquito mat is applied by appropriately heating according to the form of the formulation to vaporize the effective ingredients. The non-heating fumigant such as resin fumigant, paper fumigant, unwoven fabric fumigant, woven fabric fumigant, and sublimation tablet can be used, for example, by leaving the formulation as it is at the place to be applied, or by making a wind toward the formulation.

Examples of the place wherein the pest control composition of the present invention is applied for preventative purpose include closet, dresser, chest, wardrobe, cupboard, toilet, bathroom, storeroom, living room, dining room, warehouse, and inside a car. Further, the composition can also be applied to outside open space.

When the pest control composition of the present invention is used to livestock such as cows, horses, pigs, sheep, goats and chickens, and small animals such as dogs, cats, rats and mice, for the purpose of controlling external parasites, veterinary known methods are applied to the animals. Specifically, the formulation is administered by way of a tablet, mixing in feed, a suppository and injection (including intramuscular, subcutaneous, intravenous and intraperitoneal injections), when systemic control is intended. On the other hand, the formulation is used by way of spraying an oil solution or aqueous solution, pour-on or spot-on treatment, washing an animal with a shampoo formulation, or putting a collar or ear tag made of a resin formulation to an animal, when non-systemic control is intended. The total dosage of the present ester compound and the present cyclic compound(s) is usually in the range from 0.01 to 1000 mg per 1 kg of an animal body.

EXAMPLES

Hereinafter, the present invention will be described in more detail by way of Production Examples, Formulation Examples and Test Examples, but the present invention is not limited to only these Examples. In Examples, the term "part(s)" means part(s) by weight unless otherwise stated.

First, Production Examples of the pest control composition of the present invention will be described.

Production Examples 1 to 10

The present ester compound and any one or more of the above mentioned (i), (ii), (iii), (iv), (v), (vi) and (viii) as the present cyclic compound were mixed at a weight ratio shown in the following Table 1 to prepare a mixed composition (hereinafter, referred to as a present composition (1), (2), (3), (4), (5), (6), (7), (8), (9) or (10)).

As the present ester compound, [2,3,5,6-tetrafluoro-4-(methoxymethyl)phenyl]methyl (1R)-trans-3-(2-cyano-1-propenyl[En=1/9])-2,2-dimethylcyclopropanecarboxylate (hereinafter, referred to as a present ester compound A) was used.

TABLE 2

| | Composition (parts by weight) | | | |
|---|---|---|---|---|
| | Present ester compound A | Ethyl acetate | Xylene | Ethanol |
| Comparative composition (1) | 100 | | | |
| Comparative composition (2) | 50 | 50 | | |
| Comparative composition (3) | 50 | | 50 | |
| Comparative composition (4) | 50 | | | 50 |

Formulation Examples will be shown below.

Formulation Example 1

Into an aerosol container, 0.02 parts of the present ester compound A, 0.02 parts of any one of the present cyclic compounds (i) to (viii), and 59.96 parts of Isopar™ M (an isoparaffin solvent, manufactured by Exxon Mobil Corporation) are placed. A valve part is attached to the aerosol container, and 40 parts of a propellant (liquefied petroleum gas) is filled therein via the valve part to obtain an aerosol.

Formulation Example 2

Into an aerosol container, 0.01 parts of the present ester compound A, 0.01 parts of any one of the present cyclic compounds (i) to (viii), and 39.89 parts of Isopar™ M (an

TABLE 1

| | Composition (parts by weight) | | | | | | | |
|---|---|---|---|---|---|---|---|---|
| | | Present cyclic compound | | | | | | |
| | Present ester compound A | (i) γ-butyrolactone | (ii) N-methyl-2-pyrrolidone | (iii) N-ethyl-2-pyrrolidone | (iv) N-octyl-2-pyrrolidone | (v) 1,3-dimethyl-2-imidazolidinone | (vi) Propylene carbonate | (viii) Sulfolane |
| Present composition (1) | 1 | 99 | | | | | | |
| Present composition (2) | 30 | 70 | | | | | | |
| Present composition (3) | 50 | 50 | | | | | | |
| Present composition (4) | 50 | | 50 | | | | | |
| Present composition (5) | 50 | | | 50 | | | | |
| Present composition (6) | 50 | | | | 50 | | | |
| Present composition (7) | 50 | | | | | 50 | | |
| Present composition (8) | 50 | | | | | | 50 | |
| Present composition (9) | 50 | 2.5 | | | | | 47.5 | |
| Present composition (10) | 50 | | | | | | | 50 |

Then, production examples of comparative compositions to be used in Test Examples described later will be shown as Comparative Production Examples.

Comparative Production Examples 1 to 4

Comparative compositions containing the present ester compound A at a weight ratio shown in the following Table 2 (hereinafter, referred to as comparative compositions (1), (2), (3) and (4)) were prepared.

isoparaffin solvent, manufactured by Exxon Mobil Corporation) are placed. A valve part is attached to the aerosol container, and 60 parts of a propellant (liquefied petroleum gas) is filled therein via the valve part to obtain an aerosol.

Formulation Example 3

Into an aerosol container, 0.02 parts of the present ester compound A, 0.08 parts of any one of the present cyclic compounds (i) to (viii), and 59.90 parts of Isopar™ M (an isoparaffin solvent, manufactured by Exxon Mobil Corporation) are placed. A valve part is attached to the aerosol container, and 40 parts of a propellant (liquefied petroleum gas) is filled therein via the valve part to obtain an aerosol.

Formulation Example 4

Into an aerosol container, 0.1 parts of the present ester compound A, 0.4 parts of any one of the present cyclic compounds (i) to (viii), 3 parts of isopropyl myristate, and 56.50 parts of Isopar™ M (an isoparaffin solvent, manufactured by Exxon Mobil Corporation) are placed. A valve part is attached to the aerosol container, and 40 parts of a propellant (liquefied petroleum gas) is filled therein via the valve part to obtain an aerosol.

Formulation Example 5

Into an aerosol container, 50 parts of water, and a solution prepared by mixing 0.02 parts of the present ester compound A, 0.02 parts of any one of the present cyclic compounds (i) to (viii), 8.96 parts of Isopar™ M (an isoparaffin solvent, manufactured by Exxon Mobil Corporation), 0.8 parts of RHEODOL™ MO-60 (glyceryl oleate/propylene glycol, manufactured by Kao Corporation) and 0.2 parts of RHEODOL™ TW-O120 (polysorbate 80, manufactured by Kao Corporation) are placed. A valve part is attached to the aerosol container, and 40 parts of a propellant (liquefied petroleum gas) is filled therein via the valve part to obtain an aerosol.

Formulation Example 6

Into an aerosol container, 50 parts of water, and a solution prepared by mixing 0.02 parts of the present ester compound A, 0.08 parts of any one of the present cyclic compounds (i) to (viii), 8.90 parts of Isopar™ M (an isoparaffin solvent, manufactured by Exxon Mobil Corporation), 0.8 parts of RHEODOL™ MO-60 (glyceryl oleate/propylene glycol, manufactured by Kao Corporation) and 0.2 parts of RHEODOL™ TW-O120 (polysorbate 80, manufactured by Kao Corporation) are placed. A valve part is attached to the aerosol container, and 40 parts of a propellant (liquefied petroleum gas) is filled therein via the valve part to obtain an aerosol.

Formulation Example 7

Into an aerosol container, 0.02 parts of the present ester compound A, 0.02 parts of any one of the present cyclic compounds (i) to (viii), and 49.96 parts of NEO CHIOZOL (product name; a paraffinic solvent manufactured by Chuo Kasei Co., Ltd.) are placed. A valve part is attached to the aerosol container, and 50 parts of a propellant (1/1 mixture of dimethyl ether/liquefied petroleum gas) is filled therein via the valve part to obtain an aerosol.

Formulation Example 8

Into an aerosol container, 0.02 parts of the present ester compound A, 0.08 parts of any one of the present cyclic compounds (i) to (viii), and 49.90 parts of NEO CHIOZOL (product name; a paraffinic solvent manufactured by Chuo Kasei Co., Ltd.) are placed. A valve part is attached to the aerosol container, and 50 parts of a propellant (1/1 mixture of dimethyl ether/liquefied petroleum gas) is filled therein via the valve part to obtain an aerosol.

Formulation Example 9

Into an aerosol container, 0.1 parts of the present ester compound A, 0.4 parts of any one of the present cyclic compounds (i) to (viii), 6 parts of isopropyl myristate, and 23.50 parts of NEO CHIOZOL (product name; a paraffinic solvent manufactured by Chuo Kasai Co., Ltd.) are placed. A valve part is attached to the aerosol container, and 70 parts of a propellant (1/1 mixture of dimethyl ether/liquefied petroleum gas) is filled therein via the valve part to obtain an aerosol.

Formulation Example 10

Into an aerosol container, 40 parts of water, and a solution prepared by mixing 0.02 parts of the present ester compound A, 0.02 parts of any one of the present cyclic compounds (i) to (viii), 5.96 parts of NEO CHIOZOL (product name; a paraffinic solvent manufactured by Chuo Kasei Co., Ltd.), 3 parts of isopropyl myristate, 0.8 parts of RHEODOL™ MO-60 (glyceryl oleate/propylene glycol, manufactured by Kao Corporation) and 0.2 parts of RHEODOL™ TW-O120 (polysorbate 80, manufactured by Kao Corporation) are placed. A valve part is attached to the aerosol container, and 50 parts of a propellant (1/1 mixture of dimethyl ether/liquefied petroleum gas) is filled therein via the valve part to obtain an aerosol.

Formulation Example 11

Into an aerosol container, 40 parts of water, and a solution prepared by mixing 0.02 parts of the present ester compound A, 0.08 parts of any one of the present cyclic compounds (i) to (viii), 5.90 parts of NEO CHIOZOL (product name; a paraffinic solvent manufactured by Chuo Kasei Co., Ltd.), 3 parts of isopropyl myristate, 0.8 parts of RHEODOL™ MO-60 (glyceryl oleate/propylene glycol, manufactured by Kao Corporation) and 0.2 parts of RHEODOL™ TW-O120 (polysorbate 80, manufactured by Kao Corporation) are placed. A valve part is attached to the aerosol container, and 50 parts of a propellant (1/1 mixture of dimethyl ether/liquefied petroleum gas) is filled therein via the valve part to obtain an aerosol.

Formulation Example 12

Into an aerosol container, a solution prepared by mixing 0.1 parts of the present ester compound A, 0.4 parts of any one of the present cyclic compounds (i) to (viii), 8.5 parts of Isopar™ M (an isoparaffin solvent, manufactured by Exxon Mobil Corporation), 0.9 parts of RHEODOL™ SP-O10 (sorbitan oleate, manufactured by Kao Corporation) and 0.1 parts of RHEODOL™ TW-O120 (polysorbate 80, manufactured by Kao Corporation), and a solution prepared by mixing 69.86 parts of water and 0.14 parts of sodium benzoate are placed. A valve part is attached to the aerosol container, and 20 parts of a propellant (liquefied petroleum gas) is filled therein via the valve part to obtain an aerosol.

Formulation Example 13

Twenty eight parts of an ethylene-methyl methacrylate copolymer (methyl methacrylate content: 25% by weight, product name: Acryft WK 307, manufactured by Sumitomo Chemical Co., Ltd.), 2.5 parts of the present ester compound A, and 2.5 parts of any one of the present cyclic compounds (i) to (viii) are melted and kneaded using a closed-type pressure kneader (manufactured by Moriyama Company, Ltd.). The resulting kneaded product is hot-cut while being extruded from an extruder, to obtain a pellet. Thirty three parts of the pellet and 67 parts of linear low density polyethylene (a homopolymer of ethylene) are mixed and kneaded to obtain a resin kneaded product. Then, the resin kneaded product is extruded and stretched via a profile die for net molding from an extruder to obtain a cylindrical molded product having a diameter of about 7 cm, made of a net wherein rhombuses of about 5 mm on a side are formed (wherein the diameter of a filament forming the net is about 0.83 mm, and an opening rate of the net is 82%). The molded product is cut into a length of 20 cm to obtain a pest control composition.

Formulation Example 14

Twenty parts of the present ester compound A, 5 parts of any one of the present cyclic compounds (i) to (viii), 3 parts of NEWKALGEN PS-P (product name; naphthalenesulfonic acid, polymer with formaldehyde, sodium salt), 1 part of NEWKALGEN EX-70 (product name; sodium dioctylsulfosuccinate/sodium benzoate), 3 parts of NEWKALGEN SX-C (product name; sodium dodecylbenzenesulfonate/sodium sulfate decahydrate) (New Kalgen Series: manufactured by TAKEMOTO OIL & FAT Co., Ltd.), and 68 parts of white superior soft sugar (manufactured by Mitsui Sugar Co., Ltd.) are ground and mixed to obtain a powdery composition for an aqueous poison bait.

Formulation Example 15

To 24.96 parts of isopropyl alcohol were added 0.02 parts of the present ester compound A and 0.02 parts of any one of the present cyclic compounds (i) to (viii) and then mixed. The mixture was injected into an aerosol container. Into the aerosol container, 30.0 parts of an ammonium benzoate-ammonium buffer (prepared by adding 29% aqueous ammonia to a 1.0% w/w solution of ammonium benzoate and then adjusting the mixture to pH 8.5) was further injected to prepare an aerosol stock solution. Then, a valve was attached to the aerosol container and 45.0 parts of dimethyl ether was filled therein under pressure via the valve to obtain an aerosol.

Formulation Example 16

To 24.90 parts of isopropyl alcohol were added 0.02 parts of the present ester compound A and 0.08 parts of any one of the present cyclic compounds (i) to (viii) and then mixed. The mixture was injected into an aerosol container. Into the aerosol container, 30.0 parts of an ammonium benzoate-ammonium buffer (prepared by adding 29% aqueous ammonia to a 1.0% w/w solution of ammonium benzoate and then adjusting the mixture to pH 8.5) was further injected to prepare an aerosol stock solution. Then, a valve was attached to the aerosol container and 45.0 parts of dimethyl ether was filled therein under pressure via the valve to obtain a one-component aerosol.

Formulation Example 17

Twenty parts of the present ester compound A, 70 parts of any one of the present cyclic compounds (i) to (viii), 10 parts of [2,3,5,6-tetrafluoro-4-(methoxymethyl)phenyl]methyl 2,2-dimethyl-3-(1-propenyl)cyclopropanecarboxylate are mixed to obtain a soluble concentrate.

Formulation Example 18

Into an aerosol container, 0.02 parts of the Present ester compound A, 0.08 parts of any one of the present cyclic compounds (i) to (viii), 0.02 parts of [2,3,5,6-tetrafluoro-4-(methoxymethyl)phenyl]methyl 2,2-dimethyl-3-(1-propenyl)cyclopropanecarboxylate, 3 parts of isopropyl myristate, and 56.88 parts of Isopar™ M (an isoparaffin solvent, manufactured by Exxon Mobil Corporation) are placed. A valve part is attached to the aerosol container, and 40 parts of a propellant (liquefied petroleum gas) is filled therein via the valve part to obtain an aerosol.

Formulation Example 19

Into an aerosol container, 0.02 parts of the present ester compound A, 0.08 parts of any one of the present cyclic compounds (i) to (viii), 0.02 parts of [2,3,5,6-tetrafluoro-4-(methoxymethyl)phenyl]methyl 2,2-dimethyl-3-(1-propenyl)cyclopropanecarboxylate, 6 parts of isopropyl myristate, and 23.88 parts of NEC CHIOZOL (product name; a paraffinic solvent manufactured by Chuo Kasei Co., Ltd.) are placed. A valve part is attached to the aerosol container, and 70 parts of a propellant (1/1 mixture of dimethyl ether/liquefied petroleum gas) is filled therein via the valve part to obtain an aerosol.

Formulation Example 20

Into an aerosol container, 40 parts of water, and a solution prepared by mixing 0.02 parts of the present ester compound A, 0.08 parts of any one of the present cyclic compounds (i) to (viii), 0.02 parts of [2,3,5,6-tetrafluoro-4-(methoxymethyl) phenyl]methyl 2,2-dimethyl-3-(1-propenyl)cyclopropanecarboxylate, 8.88 parts of Isopar™ M (an isoparaffin solvent, manufactured by Exxon Mobil Corporation), 0.8 parts of RHEODOL™ MO-60 (glyceryl oleate/propylene glycol, manufactured by Kao Corporation) and 0.2 parts of RHEODOL™ TW-O120 (polysorbate 80, manufactured by Kao Corporation) are placed. A valve part is attached to the aerosol container, and 50 parts of a propellant (liquefied petroleum gas) is filled therein via the valve part to obtain an aerosol.

Formulation Example 21

Into an aerosol container, a solution prepared by mixing 0.02 parts of the present ester compound A, 0.08 parts of any one of the present cyclic compounds (i) to (viii), 0.02 parts of [2,3,5,6-tetrafluoro-4-(methoxymethyl)phenyl]methyl 2,2-dimethyl-3-(1-propenyl)cyclopropanecarboxylate, 8.88 parts of Isopar™ M (an isoparaffin solvent, manufactured by Exxon Mobil Corporation), 0.9 parts of RHEODOL™ SP-O10 (sorbitan oleate, manufactured by Kao Corporation) and 0.1 parts of RHEODOL™ TW-O120 (polysorbate 80, manufactured by Kao Corporation), and a solution prepared by mixing 69.86 parts of water and 0.14 parts of sodium benzoate are placed. A valve part is attached to the aerosol container, and 20 parts of a propellant (liquefied petroleum gas) is filled therein via the valve part to obtain an aerosol.

Formulation Example 22

To 24.88 parts of isopropyl alcohol are added 0.02 parts of the present ester compound A, 0.08 parts of any one of the present cyclic compounds (i) to (viii), and 0.02 parts of [2,3,5,6-tetrafluoro-4-(methoxymethyl)phenyl]methyl 2,2-dimethyl-3-(1-propenyl)cyclopropanecarboxylate, and then mixed. The mixture is injected into an aerosol container. Into the aerosol container, 30.0 parts of an ammonium benzoate-ammonium buffer (prepared by adding 29% aqueous ammonia to a 1.0% w/w solution of ammonium benzoate and then adjusting the mixture to pH 8.5) is further injected to prepare an aerosol stock solution. Then, a valve was attached to the aerosol container and 45.0 parts of dimethyl ether is filled therein under pressure via the valve to obtain an aerosol.

The following Test Examples show that the pest control composition of the present invention has excellent controlling effect on pests.

Test Example 1

Each of the present compositions (1) to (6) and (8) and the comparative compositions (2) and (3) was diluted and dissolved with acetone to prepare an acetone solution containing 0.00625% by weight of the present ester compound A.

Ten imagoes of housefly (*Musca domestica*) (5 male and 5 female imagoes) were released in a polyethylene cup (lower part diameter: 10.6 cm, upper part diameter: 12 cm, height: 7 cm), and the cup was closed with a 16 mesh nylon gauze. The cup was placed on the bottom of a test chamber (bottom: 46 cm×46 cm, height: 70 cm). The acetone solution (0.5 g) was sprayed from a height of 30 cm above the upper side of the cup using a spray gun (spraying pressure: 0.9 kg/cm$^2$). Immediately after spraying, the cup was taken out from the test chamber. At a given period of time after spraying, the number of knocked down insects was counted and a knock down rate was calculated (average of two runs).

The results are shown in Table 3.

TABLE 3

| | Knock down rate (%) after 30 seconds |
|---|---|
| Present composition (1) | 60 |
| Present composition (2) | 50 |
| Present composition (3) | 40 |
| Present composition (4) | 40 |
| Present composition (5) | 40 |
| Present composition (6) | 50 |
| Present composition (8) | 40 |
| Comparative composition (2) | 20 |
| Comparative composition (3) | 30 |

Test Example 2

A given amount of each of the present compositions (2) to (6) and (8) to (10) and the comparative composition (4) was diluted and dissolved with 10 parts of dichloromethane, and deodorized kerosene (Isopar™ M) was further added to prepare 100 parts of a liquid composition containing 0.00625% (wt/v) of the present ester compound A.

Ten imagoes of housefly (*Musca domestica*) (5 male and 5 female imagoes) were released in a polyethylene cup (lower part diameter: 10.6 cm, upper part diameter: 12 cm, height: 7 cm), and the cup was closed with a 16 mesh nylon gauze. The cup was placed on the bottom of a test chamber (bottom: 46 cm×46 cm, height: 70 cm). The liquid composition (0.5 ml) was sprayed from a height of 30 cm above the upper side of the cup using a spray gun (spraying pressure: 0.9 kg/cm$^2$). Immediately after spraying, the cup was taken out from the test chamber. At a given period of time after spraying, the number of knocked down insects was counted and a knock down rate was calculated (average of two runs).

The results are shown in Table 4.

TABLE 4

| | Knock down rate (%) after 45 seconds |
|---|---|
| Present composition (2) | 75 |
| Present composition (3) | 65 |

TABLE 4-continued

| | Knock down rate (%) after 45 seconds |
|---|---|
| Present composition (4) | 65 |
| Present composition (5) | 60 |
| Present composition (6) | 60 |
| Present composition (8) | 60 |
| Present composition (9) | 75 |
| Present composition (10) | 60 |
| Comparative composition (4) | 20 |

Test Example 3

A given amount of each of the present compositions (1), (3), (6) and (9) and the comparative compositions (3) and (4) was diluted and dissolved with 10 parts of dichloromethane, and deodorized kerosene (Isopar™ M) was further added to prepare 100 parts of a liquid composition containing 0.00625% (wt/v) of the present ester compound A.

Ten imagoes of German cockroach (*Blattella germanica*) (5 male and 5 female imagoes) were released in a test container (diameter: 8.75 cm, height: 7.5 cm, bottom: 16 mesh wire netted) of which inner wall was smeared with butter. The container was placed on the bottom of a test chamber (bottom: 46 cm×46 cm, height: 70 cm). The liquid composition (1.5 ml) was sprayed from a height of 60 cm above the upper side of the container using a spray gun (spraying pressure: 0.9 kg/cm$^2$). Thirty seconds after spraying, the container was taken out from the test chamber. At a given period of time after spraying, the number of knocked down insects was counted and a knock down rare was calculated (average of two runs).

The results are shown in Table 5.

TABLE 5

| | Knock down rate (%) after 0.7 minutes |
|---|---|
| Present composition (1) | 75 |
| Present composition (3) | 55 |
| Present composition (6) | 55 |
| Present composition (9) | 55 |
| Comparative composition (3) | 35 |
| Comparative composition (4) | 10 |

Test Example 4

Each of the present compositions (2) to (8) and the comparative compositions (1) and (3) was diluted and dissolved with acetone to prepare an acetone solution containing 0.0135% (wt/v) of the present ester compound A.

The acetone solution was added dropwise to a 6 cm×9 cm paper filter (manufactured by Advantec Toyo Kaisha, Ltd.) so that the present ester compound A became 100 mg/cm$^2$. Then, the paper filter was air-dried. The air-dried paper filter was folded to form a triangular cylinder having a bottom plane of a triangle of 3 cm on a side. The triangular cylinder was placed in a polyethylene cup having about 650 ml capacity. Ten imagoes of German cockroach (*Blattella germanica*) (5 male and 5 female imagoes) were placed in the cup together with absorbent cotton saturated with water. The polyethylene cup was kept for 2 hours at a temperature of 25° C. and a humidity of 60% under light condition. Then, the number of insects which were outside the triangular cylinder was counted (treated-section).

Using a triangular cylinder made of a paper filter treated with only acetone, a test was performed according to the same manner as above, and the number of insects which were outside the triangular cylinder was counted (non-treated section).

A repellent rate was calculated according to the following equation (average of two runs). The results are shown in Table 6.

Repellent rate(%)=100×{[(number of insects outside triangular cylinder at treated section)−(number of insects outside triangular cylinder at non-treated section)]/(number of insects inside triangular cylinder at non-treated section)}

TABLE 6

|  | Repellent rate (%) |
|---|---|
| Present composition (2) | 100 |
| Present composition (3) | 79 |
| Present composition (4) | 100 |
| Present composition (5) | 95 |
| Present composition (6) | 84 |
| Present composition (7) | 79 |
| Present composition (8) | 79 |
| Comparative composition (1) | 53 |
| Comparative composition (3) | 42 |

Test Example 5

Each of the present compositions (1) to (10) and the comparative compositions (1) and (4) was diluted and dissolved with acetone to prepare an acetone solution containing 0.2% by weight of the present ester compound A. The acetone solution was added dropwise to 0.5 g of a piece of an insecticidal coil (manufactured by UI Katori K.K.) so that the present ester compound A became 0.5 mg/piece. Then, the insecticidal coil was air-dried.

Ten female imagoes of common house mosquito (*Culex pipiens pallens*) were released in a cubic chamber having 70 cm sides. The insecticidal coil was ignited, placed at the center on the bottom of the chamber, and was allowed to completely burn. At a given period of time after ignition of the insecticidal coil, the number of knocked down insects was counted.

On the other hand, an acetone solution containing 20% by weight of γ-butyrolactone (hereinafter, referred to as a comparative composition (5)) was prepared. The comparative composition (5) (0.25 g) was added dropwise to 0.5 g of a piece of an insecticidal coil [manufactured by Union insecticide co., inc. (UI Katori K.K.)]. Then, the insecticidal coil was air-dried. Using the insecticidal coil, a test was performed according to the same manner as above, and the number of knocked down insects after a given period of time was counted.

The results are shown in Table 7.

TABLE 7

|  | Number of knocked down insects after 10 minutes |
|---|---|
| Present composition (1) | 6 |
| Present composition (2) | 4 |

TABLE 7-continued

|  | Number of knocked down insects after 10 minutes |
|---|---|
| Present composition (3) | 4 |
| Present composition (4) | 5 |
| Present composition (5) | 4 |
| Present composition (6) | 6 |
| Present composition (7) | 5 |
| Present composition (8) | 4 |
| Present composition (9) | 4 |
| Present composition (10) | 6 |
| Comparative composition (1) | 1 |
| Comparative composition (4) | 2 |
| Comparative composition (5) | 0 |

INDUSTRIAL APPLICABILITY

Pests can be controlled by using the pest control composition of the present invention.

The invention claimed is:

1. A pest control composition containing a combination of an ester compound represented by the formula (1):

(1)

$$\text{structure with } F, F, F \text{ substituted benzyl group bearing } CH_3OCH_2-, \text{ linked via } -CH_2-O-C(=O)- \text{ to a cyclopropane ring with } CH_3, CH_3 \text{ and } -CH=C(CN)CH_3 \text{ substituents}$$

and one or more cyclic compound(s) selected from the group consisting of N-ethyl-2-pyrrolidone, N-octyl-2-pyrrolidone, 1,3-dimethyl-2-imidazolidinone, propylene carbonate and sulfolane.

2. The pest control composition according to claim 1, wherein the weight ratio of the ester compound to the cyclic compound(s) is within the range of from 4:1 to 1:300.

3. The pest control composition according to claim 1, wherein the weight ratio of the ester compound to the cyclic compound(s) is within the range of from 1:1 to 1:100.

4. A control method of pests which comprises applying the pest control composition according to claim 1 to the pests or areas where the pests live.

5. The pest control composition according to claim 1, wherein the one or more cyclic compound(s) is propylene carbonate and/or sulfolane.

6. The pest control composition according to claim 1, wherein the one or more cyclic compounds(s) includes propylene carbonate as an essential component.

7. The pest control composition according to claim 1, wherein the one or more cyclic compound(s) is propylene carbonate.

* * * * *